United States Patent [19]

Hourahane

[11] Patent Number: 4,784,126
[45] Date of Patent: Nov. 15, 1988

[54] SURGICAL DEVICE

[75] Inventor: Donald H. Hourahane, Roodepoort, South Africa

[73] Assignee: South African Inventions Development Corporation, Pretoria, South Africa

[21] Appl. No.: 39,293

[22] Filed: Apr. 17, 1987

Related U.S. Application Data

[62] Division of Ser. No. 654,495, Sep. 26, 1984, Pat. No. 4,672,957.

[30] Foreign Application Priority Data

Oct. 4, 1983 [ZA] South Africa ............... 83/7419

[51] Int. Cl.⁴ ............................................. A61B 17/00
[52] U.S. Cl. .............................................. 128/92 YF
[58] Field of Search ........... 128/92 V, 92 YF, 92 YE, 128/92 VD, 303 B; 623/13, 20

[56] References Cited

U.S. PATENT DOCUMENTS

| | | | |
|---|---|---|---|
| 4,467,478 | 8/1984 | Jurgutis | 623/13 |
| 4,535,768 | 8/1985 | Hourahane et al. | 128/92 VD X |
| 4,585,458 | 4/1986 | Kurland | 623/13 |
| 4,590,928 | 5/1986 | Hunt et al. | 128/92 YF |

FOREIGN PATENT DOCUMENTS

| | | | |
|---|---|---|---|
| 2531580 | 1/1976 | Fed. Rep. of Germany | 623/13 |
| 1033135 | 8/1983 | U.S.S.R. | 128/92 VD |
| 634460 | 3/1950 | United Kingdom | 128/92 VD |

Primary Examiner—Michael H. Thaler
Attorney, Agent, or Firm—Bernard, Rothwell & Brown

[57] ABSTRACT

A method of surgery for attaching the end of a ligament to a bone from which it has become attached, includes drilling a passage in the bone so that the passage opens at or adjacent the position where the ligament became detached, inserting an elongated clamp through the passage, clamping the ligament with the part of the clamp which projects out of the mouth of the passage, withdrawing the clamp into the passage to draw the detached end of the ligament into the passage while tensioning the ligament, and anchoring the clamp to hold the liagment under tension to permit growth of fibrous and connective tissue in the passage to join the ligament to the bone.

10 Claims, 6 Drawing Sheets

SURGICAL DEVICE

This is a division of application Ser. No. 654,495, filed 9/26/84, now U.S. Pat. No. 4,672,957.

This invention relates to a method of surgery for reattaching the end of a ligament to a bone from which the end of the ligament has become detached.

The invention provides for a method of surgery for attaching to bone the end of a ligament which has become detached therefrom, which method comprises drilling a passage in the bone so that the passage opens out in a mouth located at or adjacent the position where the ligament became detached from the bone, drawing the detached end of the ligament via said mouth into the passage, and anchoring the end of the ligament in the passage to permit growth of fibres and connective tissue in the passage to join the ligament to the bone.

The end of the ligament may be anchored in the passage with the ligament under tension, using an elongated clamp which projects into the passage from the end of the passage remote from the mouth, the clamp clamping the end of the ligament in the passage and bearing against the bone at said end of the passage remote from the mouth to hold the ligament in tension. The clamp may be removed after the ligament has become attached to the bone in the passage by growth of fibres and connective tissue in the passage.

Drilling the passage may be by means of a bone drill whose bit extends through a drill guide attached to a probe, the probe being inserted into soft tissue adjacent the bone to locate and align the drill guide relative to the bone.

The drill guide and probe may form part of a device as described above, and the passage may accordingly be a straight passage drilled into the bone from the side of the bone remote from the mouth. Instead, the passage may comprise two portions drilled into the side of the bone where the mouth is located and intersecting below the surface of the bone, the drill being used to drill the portions successively through two inclined passages in the drill guide, which passages have axes which intersect at a position spaced from the drill guide, the drill guide having a head and a handle as described above, being used for this purpose.

In typical knee surgery the device of the invention will be used in conjunction with other surgical instruments, of an ancillary nature, for knee ligament repair.

The invention will now be described, by way of example, with reference to the accompanying diagrammatic drawings, in which.

Figure 1:
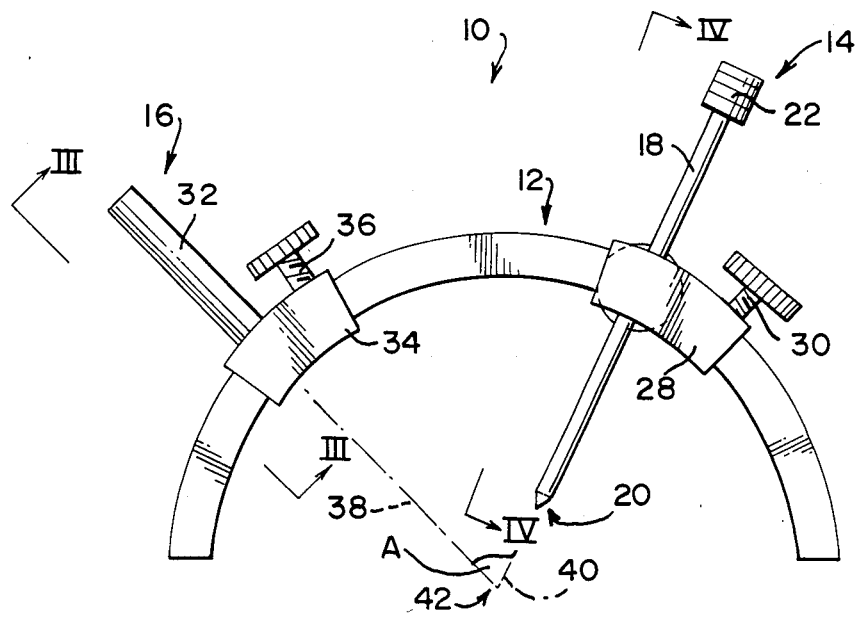
FIG. 1 shows a side elevation of a device in accordance with the invention.

In the drawings, reference numeral 10 generally designates a surgical device for use in the present invention, and suitable for surgery performed on a human knee joint. The device is of stainless steel construction.

The device 10 comprises a bracket 12, a probe generally designated 14, and a drill guide generally designated 16. The probe 14 and drill guide 16 are mounted on the bracket 12.

Figure 2:
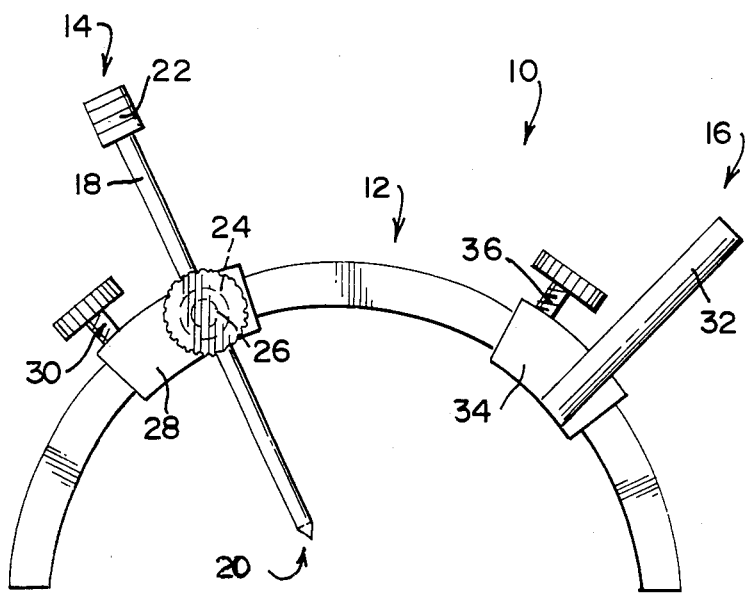
FIG. 2 shows the opposite side elevation of the device of FIG. 1.
Figure 3:
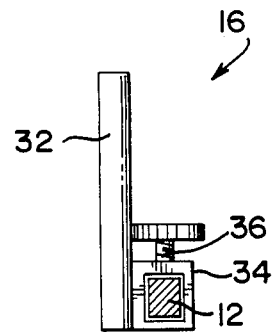
FIG. 3 shows a section of the device of FIG. 1, in the direction of line III—III in FIG. 1.
Figure 4:
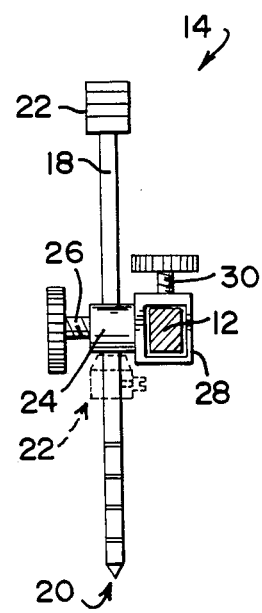
FIG. 4 shows a section of the device of FIG. 1, in the direction of line IV—IV in FIG. 1.

The bracket 12 is sector-shaped in side elevation as shown in FIGS. 1 and 2 and is of substantially constant substantially rectangular cross-section as shown in FIGS. 3 and 4. A convenient method of obtaining the bracket 12 in practice is to slice off an extremely short length from a stainless steel pipe having the radius of curvature desired for the bracket 12 and a length equal to the thickness in the axial direction of the eventual bracket 12. The slice of pipe is then cut at appropriate positions along its circumference to provide the ends of the bracket 12, which is then in the shape of a part-circular limb.

Turning to the probe 14, this comprises a straight in the form of a pin 18 having a pointed end at 20 and a head 22 at its opposite end. In FIGS. 1 and 2, the pointed end 20 is shown pointing radially inwardly relative to the curvature of the bracket 12. The pin 18 fits longitudinally slidably through a diameterical passage through a tubular guide 24. One end of the axial passage of the guide 24 is threaded and is provided with an associated set screw 26 having a knurled head, and screwable into said threaded part of said central passage, to engage and releasably lock the pin 18 in position in the guide 24. Screwing the set screw 26 outwardly releases the pin 18 and permits it to slide through said diametrical passage through the guide 24, radially relative to the curvature of the bracket 12.

Instead of being fixed to the outer end of the pin 18, the head 22 may be annular and slidable along the pin 18, and provided with a grub screw whereby it can be locked releasably in position at various places along the length of the pin. The head 22 can act as a stop for limiting penetration of the pin 18 through the guide 24, either outwardly of the guide 24 of inwardly thereof, as shown in FIG. 4 in broken lines. Furthermore, the pin 18, or at least its portion near its end 20, can be graduated with a scale as shown in FIG. 4, to assist a user in assessing its depth of penetration into the site of an operation.

The opposite end of the guide 24, remote from the set screw 26, is rigidly fast with an arcuate support 28 which is substantially rectangular in cross-section, and which has an arcuate passage extending lengthwise along it, also of substantially rectangular cross-section. The curve of the support 28 and its passage, which receives the bracket 12, correspond substantially with the curvature of the bracket 12, so that said support 28 can slide longitudinally along said bracket 12. The bracket 12 is a close sliding fit in the passage of the support 28, and the wall of the support which is radially outermost relative to the curvature of the bracket 12 has a threaded passage which receives a set screw 30 provided with a knurled head.

Turning now to the drill guide 16, this comprises a tubular straight sleeve 32 which is mounted fixedly on a support 34 similar to the support 28. The support 34 is thus similarly of arcuate shape, being substantially rectangular in cross-section and having a substantially rectangular passage therethrough, which in turn also slidably receives the bracket 12 with a close sliding fit. The support 34 similarly also has a set screw 36 having a knurled head, and passing through a threaded passage in its wall which is radially outermost relative to the curvature of the bracket 12. The sleeve 32 is fast with the support 34 on the same side of the bracket 12 as the pin 18, and the sleeve 32 and pin 18 are arranged such that their respective polar axes 38, 40 are radially aligned relative to the curvature of the limb 12 and intersect at the central axis 42 of the bracket 12, about which the bracket 12 is curved, said polar axes of the sleeve 32 and pin 18 being located in a common flat plane. The arrangement is such that by releasing and locking the set screws 30, 36, the support 28, 34 can be moved along the bracket 12 and locked in position with various spacings therebetween. Changing the spacing between the supports 28 and 34 automatically alters the attitude of the sleeve 32 relative to that of the pin 18, i.e. it automatically varies the angle A between said axes 38 and 40. Nevertheless, regardless of the positions of the supports 28, 34 on the bracket 12, said axes 38 and 40 will always intersect at the axis 42 of the bracket 12, and will always remain in said common flat plane which is normal to said axis 42.

It should be noted with regard to the supports 28 and 34, that they can be formed in a fashion similar to the bracket 12, i.e. a sector is cut of a suitable length from a pipe wall and a passage is formed therein of a suitable curvature. Thus a suitable groove can be turned or milled in the inside or concave part of the sector, and this groove can be closed off to form the passage. The engagement between the limb 12 and the supports 28 and 34, by virtue of the rectangular cross-section of the limb 12 and the rectangular cross-sections of the arcuate passages in the supports, is such to prevent rotation of either of the supports around the limb 12 when they are unlocked from the limb. It should also be noted that the supports 20 and 34 can slide off either end of the limb 12 when their respective set screws 30, 36 are released.

In use, e.g. during surgery for ligament repair on a human knee joint, it is often desirable to drill one or more passages in the bone of the knee joint, in one or more positions which are not easily visible, if at all, to a surgeon. During such a surgical operation, the pin 18 of the probe 14 will be driven into the soft tissue of the knee joint in the direction of its pointed end 20, to assume a position in which it is visible, either directly or indirectly via an arthroscope, to the surgeon. This can be done with the support 28 in position on the bracket 12, or, for convenience, the bracket 12 can be removed from the support 28, during insertion of the pin 18. Naturally, the position of the pin 18 in its guide 24 can be adjusted, as convenient, by use of the set screw 26.

When the pin 18 has been inserted to the desired depth into the knee joint, and its pointed end 20 is visible to the surgeon, and the bracket 12 has been inserted in the support 28 and locked thereto by the set screw 30 if necessary, the drill guide 16 will be moved to the appropriate position, relative to the probe 14 along the bracket 12, and locked into positions by means of the set screw 36.

The device 10 will then be manipulated as necessary, by rotating it about the axis 40 of the pin 18, until the guide 16 is at the desired position and has its sleeve 32 pointing in the desired direction for a passage to be drilled in the appropriate position and in the desired direction by a drill passing through the sleeve 32 of the guide 16.

From a knowledge of the geometry of the device and the human knee, and by holding the device 10 firmly in position during the drilling, a surgeon can quickly and easily ensure that a hole is drilled in the proper position and direction, and to the necessary depth, by monitoring the position of the end 20 of the pin 18 and the depth to which the drill bit has entered the sleeve 32. Judgement and skill required for a surgeon to drill such holes in the proper places are thus substantially reduced by use of the device of the present invention, promoting more accurate, and hence safer and more successful, surgical procedures. The device itself is simple, robust, durable and extremely simple to operate, and the time between insertion of the pin into the knee and the start of drilling need be no more than a few seconds. Furthermore, the use of the device causes relatively little trauma, and the passage formed in the soft tissue by the pin 18 will generally require little if any suturing. It is thus in principle possible, using the device, to perform a knee ligament repair operation with an arthroscope, in suitable cases, where there is no damage to the capsular mass of the interior of the knee joint, by anything other than such instruments as are required to pass along the passages necessary for the probe, arthroscope and drill bit.

Figure 5:
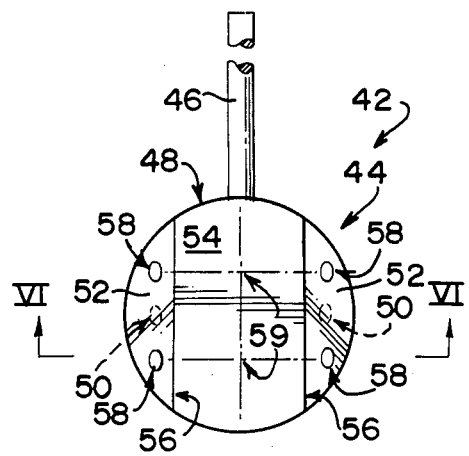
FIG. 5 shows a plan view of a drill guide which forms, with the device of FIGS. 1 to 4, part of a kit according to the invention.
Figure 6:
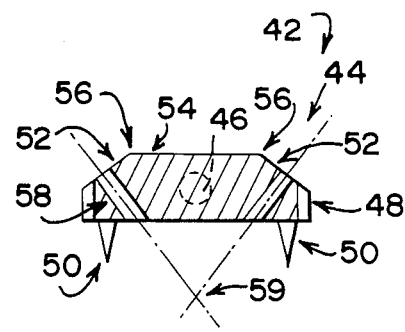
FIG. 6 shows a section along line VI—VI in FIG. 5.

Turning to FIGS. 5 and 6 of the drawings, reference numeral 42 generally designates a further drill guide for use in accordance with the invention, as part of a kit of which the device of FIGS. 1 to 4 also forms part. The guide 42 comprises a head 44 in the form of a flattened surgical steel disc having a handle in the form of a stem 46 projecting radially from its cylindrical surface 48. Opposite sides of the disc 44 are parallel, and one side thereof has a pair of parallel pointed locating probes in the form of pins 50 projecting normally therefrom, the pins 50 being diametrically opposed from each other and being spaced on opposite sides of the longitudinal axis of the stem 46, which is straight, as seen in FIG. 5.

The opposite side of the disc 44 is provided with two chamfered or bevelled zones 52 which are the same size as each other, and which slope downwardly and oppositely outwardly at the same slope from a central raised zone 54 as shown in FIG. 6. The lines 56 where the zones 52 intersect the zone 54 are parallel to the stem 46.

Two pairs of straight passages 58 are provided through the disc 44, the one pair being on the opposite side of the pins 50, when seen in FIG. 5, from the other pair. Each pair of passages 58 has one end of one passage opening out of one of the bevelled zones 52, and the other passage of the pair opening out of the other zone 52.

The passages 58 of each pair are inclined relative to each other to converge downwardly towards one another as shown in FIG. 6, so that the ends of the passages 58 of a pair, where they open out through the side of the disc 44 carrying the pins 50, are closer together to each other than their ends which open respectively through the bevelled zones 52. The spacing and inclination between the passages 58 of each pair, are the same in both pairs. The passages 58 of each pair are each normal to the respective bevelled zones 52 through which they open and the axes of the passages of each pair are aligned so that projections of the passages intersect as shown at 59 in FIGS. 5 and 6 at a position spaced from the head and in register with the axis of the stem 46, when seen in FIG. 5, on the side of the head towards which the pins project. Each passage 58 of each pair is parallel to the passage of the other pair which opens through the same zone 52.

Figure 7:
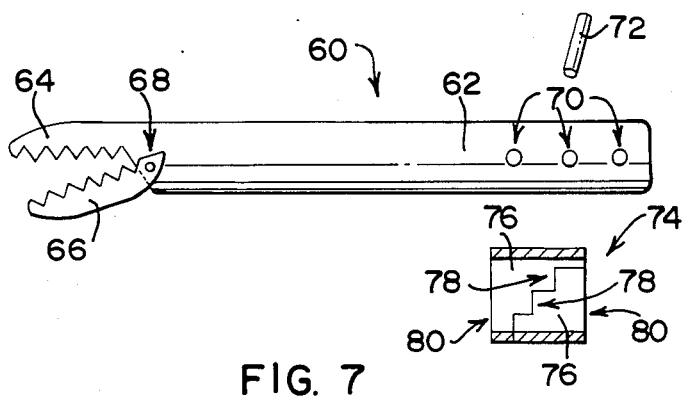
FIG. 7 shows a side elevation of a suture clamp forming part of the kit.

Turning to FIG. 7, reference numeral 60 generally designates an elongated crocodile-type clamp also forming part of the aforementioned kit, in accordance with the invention. The clamp 60 comprises a cylindrical stem 62 having, at one end thereof, a fixed toothed jaw 64, integral therewith, which co-operates in use with a movable toothed jaw 66 which opposes it, and which is pivoted to the stem 62 at 68. The opposite end of the stem 62 is provided with a number of longitudinally spaced diametrically extending parallel extending passages 70 therethrough, parallel to the axis of the pivot 68.

FIG. 7 is shown as a somewhat exploded view, and includes a pin 72 receivable in the passages 70, and a double faced stepped cam 74 is, as with the pin 72, shown adjacent the passages 70. The cam 74 comprises two cylindrical members 76 having stepped end faces 78 which in use engage one another. Depending on which steps of the one end face 78 engage which steps of the other end face 78, the spacing between the opposite end faces 80 of the cylindrical members can be altered, changing the engagement between the steps involving rotation of the one cylindrical member 76 relative to the other. As will be described in more detail hereunder, the pin 72 fits through one of the passages 70, and the cam 74 fits around the stem 62 as a spacer between the pin 72 and the surface of bone around the mouth of a passage into which the stem 62 passes.

Figure 8:
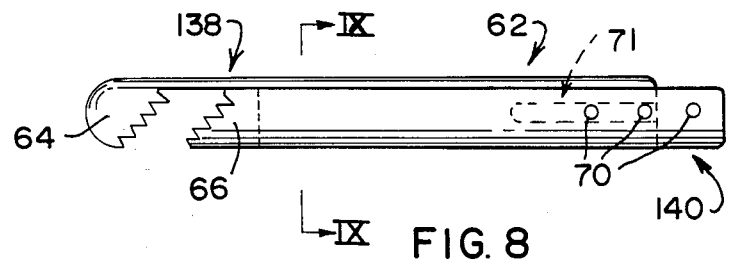
FIG. 8 shows a side elevation of another suture clamp for the kit.
Figure 9:
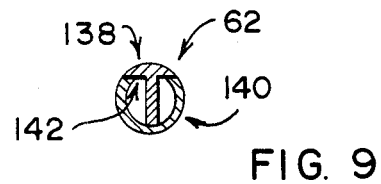
FIG. 9 shows a section along line IX—IX in FIG. 8.
Figure 10:
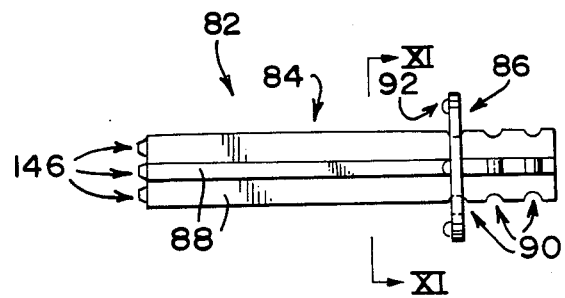
FIG. 10 shows a side elevation of another suture clamp for the kit.

The same reference numerals are used for the same or similar parts in FIGS. 8 and 9 as in FIG. 7. Thus there is an elongated clamp having a fixed jaw 64 and a movable jaw 66, at one end of a stem 62. However, instead of the movable jaw 66 being pivotable, it is longitudinally slidable relative to the jaw 64, the stem 62 comprising a part 138 which is roughly T-shaped in cross-section as shown in FIG. 9 and which carries the jaw 64. The other part of the stem 62, designated 140, is hollow and part cylindrical in cross-section as shown in FIG. 10, having a slot 142 along its length which receives the stem of the T of the part 138. The part 140 carries the jaw 66, and the parts 138, 140 are longitudinally slidable relative to each other. The parts 138, 140 fit together, so that the stem 62 is externally substantially cylindrical, and of a diameter such as to be a sliding fit in the passage in bone for which it is intended.

Figure 11:
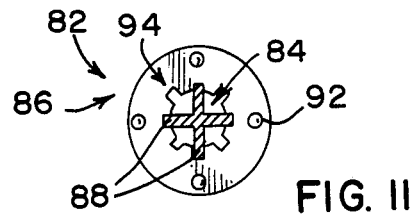
FIG. 11 shows a section along line XI—XI in FIG. 10.

Referring now to FIGS. 10 and 11, reference numeral 82 generally designates another clamp forming part of the kit in accordance with the invention. The clamp 82 comprises a cruciform stem 84 and an annular disc 86. The stem 84 has four radially outwardly projecting equally circumferentially spaced ribs 88 each of which has a number of longitudinally spaced radially outwardly facing notches 90 at one end thereof, the notches of the ribs being in register with one another, so that corresponding notches on the ribs can receive the disc 86, as described hereunder.

The disc 86 has on one side thereof a concentric ring of four equally circumferentially spaced spacers in the form of small knobs 92, and the central opening of the disc 86 has four equally circumferentially spaced radially inwardly facing notches 94.

The stem 84 passes through the central opening of the disc 86, with the knobs 92 on the side of the disc 86 which faces the end of the stem 84 remote from the notches 90. When the notches 94 are aligned respectively with the ribs 88, the stem 84 is longitudinally slidable through the disc 86. When the disc 86 is in register with a group of four of the notches 90 which are in register with one another, the disc 86 can be rotated relative to the stem 84, the periperhy of the central opening through the disc 86, between the notches 94, being received in said group of four notches 90, to permit such rotation. Engagement of the periphery of the inner opening through the disc 86 and the sides of said notches 90, then locks the disc 86 longitudinally in position relative to the stem 84. Correspondingly, when the disc 86 is not in register with a group of four of the notches 90, engagement between the ribs 88 and the notches 94 prevents rotation of the disc relative to the stem.

Figure 12:
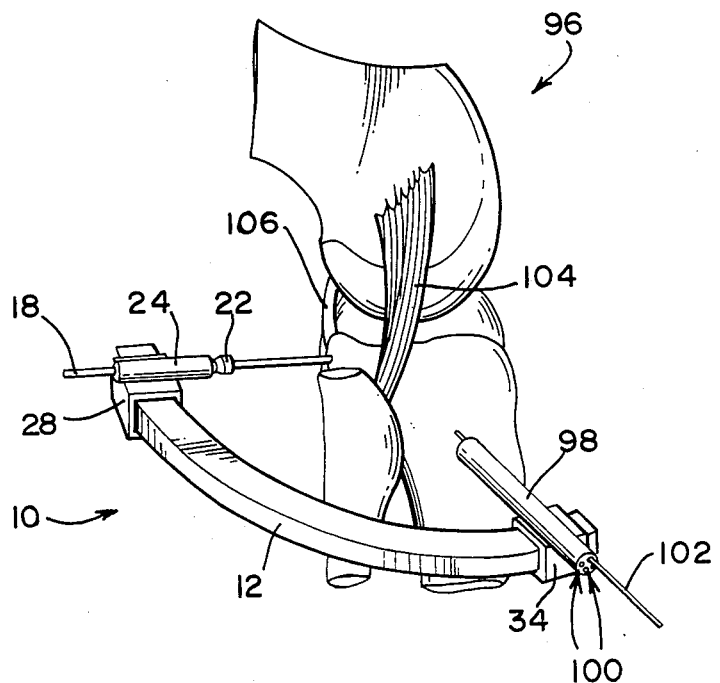
FIG. 12 shows a schematic view of a modified form of the device of FIGS. 1 to 4 in use.

FIG. 12 generally illustrates a slightly modified form of the device of FIGS. 1 to 4 in use to drill a pattern of holes in a knee joint 96, to reach the posterior attachment of the posterior cruciate ligament from a posterior lateral aspect. Unless otherwise specified, the same reference numerals are used as in FIGS. 1 to 4 of the drawings for the same parts.

It should be noted that in FIG. 12 item 24 is a tube without a set screw 26, and item 22 is annular and slidable along pin 18, as shown in broken lines in FIG. 4. Furthermore, the tubular sleeve drill guide 32 of FIGS. 1 to 4 has been replaced by a rod 98 which has a concentric ring of four parallel equally circumferentially spaced passages 100 passing therethrough, in a square pattern. These passages 100 also act as drill guides and permit a pattern of holes or passages to be drilled in bone, and it should be noted that when the first passage has been drilled in bone, a locating pin 102 can be inserted through the associated passage 100 into said passage which has been drilled in bone, better to fix and locate the device 10 relative to the knee joint 96.

Figure 13:
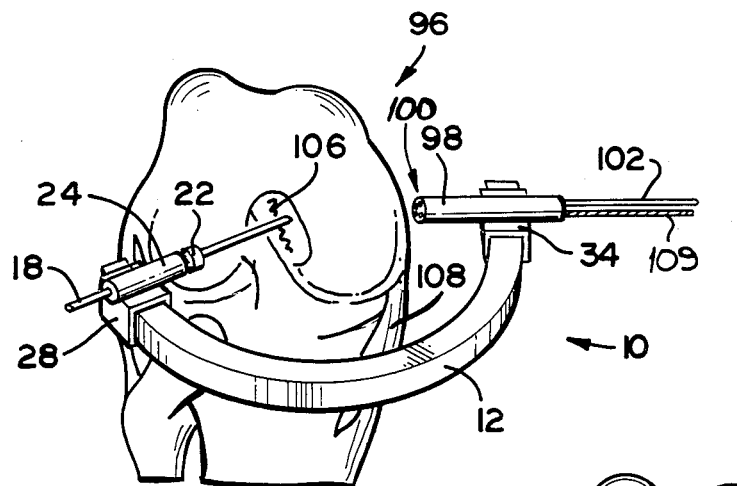
FIG. 13 shows another schematic view of the device of FIGS. 1 to 4 in use.

FIG. 13 is similar to FIG. 12, except that it illustrates the device 10 being used in a different fashion on a knee joint 96. Once again, the same reference numerals are used as in FIG. 12, unless otherwise specified. Whereas FIG. 12 shows the lateral colateral ligament at 104 and the posterior cruciate ligament at 106, FIG. 13 shows the medial colateral ligament at 108, the posterior cruciate ligament again being shown at 106. FIG. 13 illustrates the use of the device 10 to position a pattern of four holes or passages into the medial attachment point of the posterior cruciate ligament. For clarity of illustration the patella and patella tendon have been omitted, and it should be noted that the device 10 can be positioned relative to the knee to provide for simultaneous attachment of the medial colateral ligament 108, during substantially the same procedure. A drill bit 109 is shown entering the rod 98 via one of its holes 100.

Figure 14:
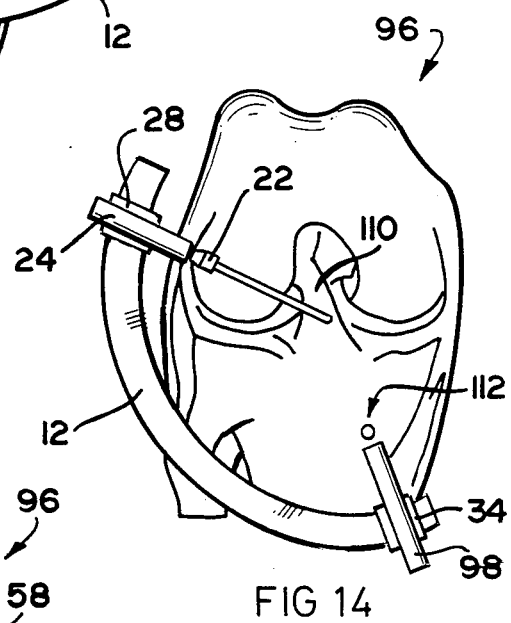
FIG. 14 shows another schematic view of the device of FIGS. 1 to 4 in use.

FIG. 14 shows yet another use of the device of FIGS. 1 to 4 on a knee joint 10, and the device 10 is illustrated in position to provide a hole or passage into the substance of the anterior cruciate ligament 110, via bone at 112 to create a path for carbon fibre or other ligament reinforcement to be inserted for connection to said ligament 110.

Figure 15:
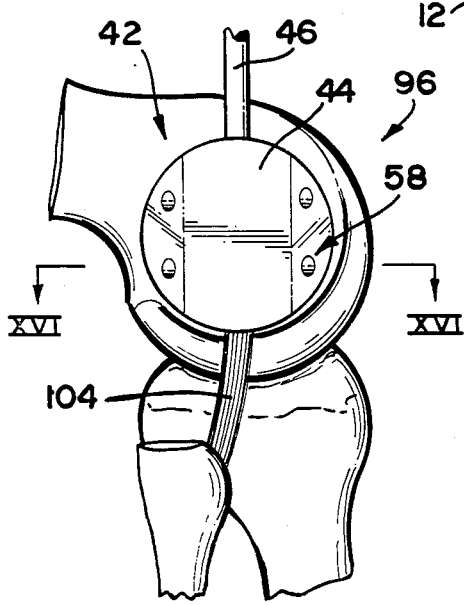
FIG. 15 shows a schematic view of the instrument of FIGS. 5 and 6 in use.
Figure 16:
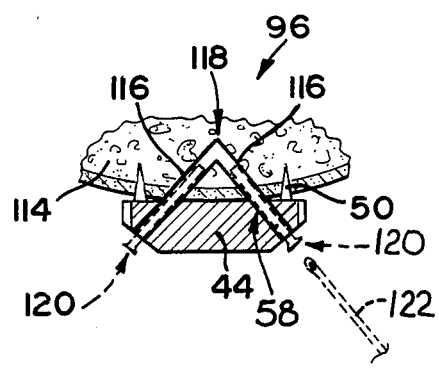
FIG. 16 shows a section along line XVI—XVI in FIG. 15.

Turning now to FIGS. 15 and 16, reference numeral 96 again indicates a knee joint or part thereof, and reference numeral 42 indicates a drill guide in accordance with FIGS. 5 and 6, the same parts being designated by the same numerals, as in FIGS. 5 and 6. As shown in FIGS. 15 and 16, the guide 42 is held in position against a bone 114 of the knee 96, by means of the stem 46, the pins 50 engaging said bone to locate the disc 44 in position. A drill is then used, via the passages 58, to drill two pairs of passages 116 in said bone 114, the passages 116 of each pair intersecting as at 118.

In use, after drilling, the guide 42 is removed, and a tube 120 is inserted into each of the passages 116 of an intersecting pair (shown partially inserted and in broken lines in FIG. 16). The tubes 120 will be inserted after removal of the guide 42, fully into the passages 116, and the tubes 120 will be of the same length or longer than the passages. A suture is then inserted via one of a wire or formed by the eye of a needle 122 inserted through the other tube 120. The eye is used to engage the suture, to withdraw it so that the suture is threaded through the intersecting passages 116. This suture is then used to suture the damaged lateral colateral ligament 104, at or adjacent its end, to the mouth of said intersecting pair of passages where they emerge from the bone, the passages, naturally having been drilled in the appropriate position, by appropriate location of the guide 42 during drilling. This procedure is repeated with the other pair of intersecting passages 116, which also have a suture passing therethrough which is attached at or adjacent the end of said ligament 104, firmly to sew the ligament into position. This permits the two looped sutures to be supported by a bridge of bone overlying said passages. In time the ligament 104 will attach itself to the bone at the mouth of the passages, and can also penetrate into said passages, where it can be anchored by connective or fibrous tissue, which grows into and invades said passages, to close them.

Figure 17:
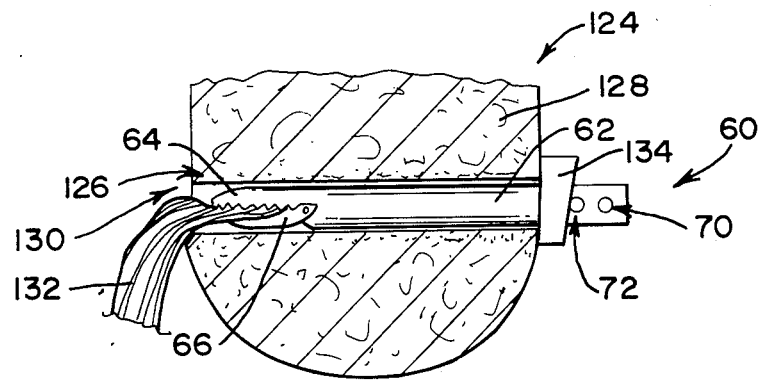
FIG. 17 shows a schematic view of the clamp of FIG. 7 in use.

Turning now to FIG. 17, reference numeral 124 generally designates the clamp of FIG. 7 in use. A passage 126 has been formed in bone 128, with one of the opening from the passage 126 being located at 130, where a ligament 132 is normally anchored, but where it has become detached. The clamp 60 is inserted, jaws first, from the opposite end of the passage, the stem 62 being a sliding fit in said passage. Insertion is until the jaws project at 130, where they can be opened and where the end of the ligament can be inserted between the jaws. Withdrawal of the clamp through the passage 126 forces the jaws together to grip the ligament, after which the clamp 60 can be anchored in position. This can be effected, as shown in FIG. 17, simply by passing a U-shaped wedge 134 under the pin 72 around the stem 62, so that engagement between the wedge and pin holds the clamp 60 suitably in position, appropriately to tension the ligament 132, said pin 72 being inserted through one of the passages 70, as appropriate, to give said tension.

When the ligament 132 has attached itself to the bone 128 at and/or inside the mouth 130 of the passage 126, the clamp 60 can be removed by reaming it out of or otherwise removing it from the passage 126, which eventually fills with connective or fibrous tissue, or, if made of sufficiently biocompatable or biodegradable material, the clamp 60 can merely be left in position permanently.

It will be appreciated that, instead of using the wedge 134, the cam 74 of FIG. 7 can be used, likewise fitting between said bone 128 and the pin 72, the parts of the cam 74 being rotated so that the appropriate steps thereon engage to provide the desired tension for the ligament 132.

The wedge 134 and pin 72, or the stepped cam 74 and the pin 72, as the case may be, act as stop means engageable with the clamp at a plurality of positions along its length, and extend transversely relative to the clamp in use to engage the bone 128 at the end of the passage 126 remote from the mouth 130.

Use of the clamp of FIGS. 8 and 9 is essentially similar to the use of the clamp 60 of FIG. 7. In use, the parts 138 and 140 are merely slid relative to each other to space the jaws 64, 66 apart, to receive the ligament, after which they are slid to clamp said jaws together, with the ligament therebetween. Use is otherwise similar to that described in FIG. 17, the end of the stem 62 remote from the jaws being appropriately anchored in use, e.g. by the part 140 having passages 70 as shown in FIG. 7 for a pin 72 for use with a cam 74 (FIG. 7) or wedge 134 (FIG. 17). In this regard the limb of the T of the part 138 has a slot 71 to permit the pin 72 to pass therethrough.

Figure 18:
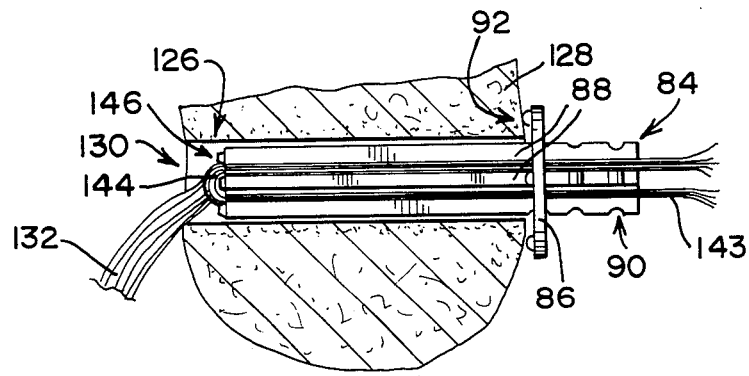
FIG. 18 shows a schematic view of the clamp of FIG. 10 in use.

Turning now to FIG. 18 the clamp of FIGS. 10 and 11 is shown in use, the same reference numerals again being used for the same parts, unless otherwise specified. In FIG. 18 a passage 126 is again shown having been drilled in bone 128 by the device 10 of FIGS. 1 to 4. The stem 84 of the clamp of FIGS. 10 and 11 is shown inserted into the end of the passage 126 remote from its mouth 130. Flexible material 143, such as one or more sutures or the like is looped longitudinally around the stem 84, to provide a loop at 144, the flexible material extending along the passage 126 in the spaces between the ribs 88 of the stem 84. The end of the ligament to be attached at 130 is then pulled through the loop 144, and the loop is pulled tight against said end of the stem 84, to clamp the ligament against it. The ends of the sutures 143 outside the passage 126 remote from the mouth 130 are then knotted together or otherwise suitably anchored to maintain the loop 144 tight and under tension to clamp the ligament tightly in position.

It will be appreciated that the ends of the ribs 88 remote from the notches 90 can each have a truncated rounded pin projecting axially outwardly therefrom, as shown at 146 in FIG. 10. The ends of these pins engage the ligament, and assist the loop 144 in clamping it to the end of the stem 84. The stem 84 is then withdrawn through the passage 126, and the disc 86 is inserted longitudinally over the opposite end of the stem 84, the knobs 92 engaging the outer surface of the bone 128 at the end of the passage 126 remote from its mouth 130, the disc 86 being engaged as described above with the appropriate set of four notches 90 to provide the ligament with the required tension. The disc 86 thus acts as stop means engageable with the stem 84 at a plurality of positions along the length of the clamp and extends transversely relative to the stem 84 to engage bone 128 at the end of the passage 126 remote from the mouth 130.

In this regard it will be appreciated that such ligaments, if they have been damaged and have become detached, at least partially, from their normal anchorages, will have undergone some irreversible stretching, so that to obtain the correct tension, it will usually be necessary to pull them at least partially into the passage in question, and this applies also with reference to FIG. 17.

With regard to FIG. 18, it should be noted that the knobs 92 space the disc 86 from the bone 128. This means that the ligament 132 can grow into attachment with the bone 128 in the passage 126, and that fibrous or connective tissue can extend from the ligament along the passage, between the ribs 88, and out of the bone at the end of the passage remote from the mouth 130, where such connective or fibrous tissue can spread out under the disc 86 and can attach itself to the outer surface of the bone there. Thus, in essence, the ligament can be regarded as passing through the bone along said passage 126, to be anchored at the opposite end of the passage, remote from its normal point of attachment.

Figure 19:
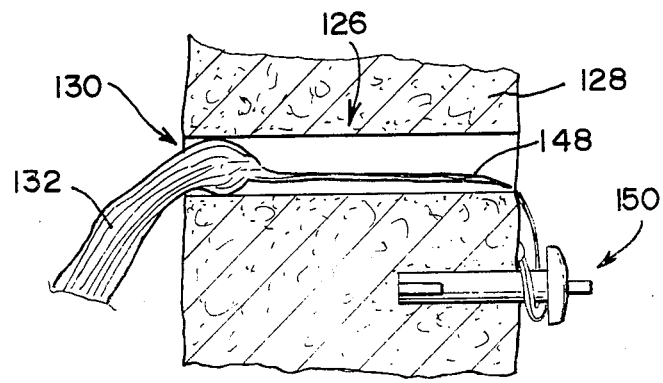
FIG. 19 shows a schematic view illustrating a further surgical procedure associated with the invention.

With reference to FIG. 19, the same reference numerals are used to designate the same parts as in FIGS. 17 and 18, unless otherwise specified. In FIG. 19, the situation is shown where sutures 148 are attached to the end of the ligament 132, and are used to draw it into the passage 126 via its mouth 130. The sutures are then anchored to the bone adjacent the opposite end of the passage, under the appropriate tension, by a stud 150. Once again the ligament 132 can grow into attachment with the bone 128, by means of fibrous and connective tissue along the passage 126 and outside the mouth of the passage 126 remote from the mouth 130.

It should be noted that the device 10 of FIGS. 1 to 4 and the guide 42 of FIGS. 5 and 6 can be used together to create a desired pattern of holes around the attachment points of ligaments in knee surgery, so that sutures or the like as described above can be used to pull a broken or damaged ligament back into place and then to suture it down. In this regard it should be noted that the device 10 has particular versatility, in that it can be used to ensure, as far as possible, that the passages drilled in bone miss other ligaments or vital organs during the drilling. Thus, within limits, the most suitable available drill path can be chosen by the surgeon. In general it is contemplated that the device of FIGS. 1 to 4 will be used for repairing anterior and posterior cruciate ligaments, and that the guide of FIGS. 5 and 6 will be used for repairing medial and lateral colateral ligaments. In this regard it should be noted that, if desired, the guide 42 can be used together with an adaptor (not shown) in the form of a metal plate having openings or short passages therethrough arranged in the same pattern and at the same angles as the passages 58 in the disc 44, to act as guides for the tubes 120 (see FIG. 16), when the guide 42 has been removed and the tubes 120 are inserted into bone.

The device 10 of FIGS. 1 to 4 can be used to drill patterns of two, four, and less commonly three holes, when the rod 98 has four passages 100 (FIGS. 12 and 13) and with a single passage through the sleeve 32 (FIGS. 1 to 4) a large hole can be drilled in bone for admission of carbon fibre or other suitable fibre tows for ligament replacement. These devices 10 and 42 will also typically, as described above, be used when appropriate together with the various clamps of FIGS. 7 to 11.

It should further be noted that by appropriate placing of passages, several ligaments can be repaired simultaneously, e.g. by drawing the ends of such ligaments, into opposite ends of passages formed in bone. Thus in principle it is possible to repair a posterior cruciate ligament together with a medial colateral ligament, and it is possible to repair an interior cruciate ligament simultaneously with a lateral colateral ligament.

Prior methods of ligament repair known to the applicant involve suturing damaged ligaments against the bone, at or near the site where they were originally attached. Such repairs are notoriously fragile, and difficult to effect, and the present invention provides a kit and the devices comprising it, which form passages in bone for this purpose, into which a damaged end of a ligament can be pulled, e.g. by an appropriate clamp as described above, or by a suture. This provides the important advantage that the ligament can be appropriately tensioned, to take up such slack as may have been caused by stretching the ligament, when it is damaged, past its elastic limit. The kit provides for drilling in particular, but also for insertion of the various clamps and other devices, and for tensioning and the like, to be effected from positions generally outside the knee joint, and the invention also promotes the use of arthroscope procedures, to reduce damage to the capsular mass as far as possible.

The instrumentation provided promotes accurate drilling of passages in bone, and facilitates tensioning of ligaments being repaired, so that such ligaments extend under the appropriate tension for regeneration, and in their proper paths in the knee, to avoid long term damage arising from unnatural movement of the knee, which can be caused by attaching ligaments in the wrong places. Although gripping the damaged ligaments with sutures or clamps may reduce their blood supply, it is contemplated that this will be re-established by connective tissue which also assists in holding the ligament in the bone into which it has been pulled. Inserting carbon fibres to reinforce damaged ligaments, so that the fibres extend along the ligament paths, can also encourage the regeneration of damaged ligaments, as such carbon fibres have been found to encourage such regeneration, in knee ligament replacement and prosthesis.

If the various clamps shown in the drawings are not biodegradable or biocompatible so that they can be left permanently in position, they must be removed after recovery from the operation. In this regard, although the clamps can be drilled or reamed out, to leave a passage which later is filled by regenerative growth, it is preferable to be able to pull them out of the bone, and in this regard, it is to be noted that the clamp of FIGS. 10 and 11 is particularly advantages, as its cruciform cross section means that it can be pulled out of the passage in which it is located, with relatively little disturbance of the tissue remaining there, which can regenerate afterwards.

I claim:

1. A method of surgery for attaching to bone the end of a ligament which has become detached therefrom, which method comprises drilling a passage in the bone so that the passage opens out at a mouth located at or adjacent the position where the ligament became detached from the bone, inserting an elongated clamp into the passage from the end of the passage remote from the mouth so that the clamp projects out of said mouth, clamping the part of the clamp which projects out of the mouth to the ligament, withdrawing the clamp in a direction along the passage away from the mouth to tension the ligament while drawing the detached end of the ligament via said mouth into the passage, and anchoring the clamp in the passage so that the detached end of the ligament is located in the passage with the ligament under tension, to permit growth of fibrous and connective tissue in the passage to joint the ligament to the bone.

2. A method as claimed in claim 1, in which the anchoring of the clamp in the passage is by continuing said withdrawing until the clamp projects out of the end of the passage remote from the mouth and engaging the clamp where it projects out of the end of the passage remote from the mouth by means of an anchor which bears against the bone at said end of the passage remote from the mouth to hold the ligament in tension.

3. A method as claimed in claim 2, in which the anchoring of the clamp comprises inserting a wedge between the anchor and the bone at the end of the passage remote from the mouth.

4. A method as claimed in claim 3, in which the clamp is removed after the ligament has become attached to the bone in the passage by growth of fibrous and connective tissue in the passage.

5. A method as claimed in claim 4, in which the clamp has a stem which is cruciform in cross-section, and the removing of the clamp is by pulling it axially out of the passage from the end of the passage remote from the mouth.

6. A method as claimed in claim 1, in which drilling the passage is by means of a bone drill whose bit extends through a drill guide attached to a probe, the probe being inserted into soft tissue adjacent the bone to locate and align the drill guide relative to the bone.

7. A method as claimed in claim 1, in which the passage is a straight passage drilled into the bone from the side of bone remote from the mouth.

8. A method as claimed in claim 1, in which the clamp has a pair of opposed jaws which are movable relative to each other between an open position and a clamped position, clamping the part of the clamp which projects out of the mouth of the passage to the ligament being by positioning the ligament between the jaws and moving the jaws into their clamped position.

9. A method as claimed in claim 8, in which moving the jaws into their clamped position is effected by the withdrawal of the clamp along the passage, contact between the jaws and the bone at the mouth of the passage acting to urge the jaws automatically into said clamped position.

10. A method as claimed in claim 1, in which clamping the part of the clamp which projects out of the mouth of the passage to the ligament is by pulling the ligament through a loop of flexible material at the end of the said outwardly projecting part of the clamp, and pulling said loop tightly around the ligament to clamp it against the end of the clamp, the flexible material then being tied to maintain the loop tight and under tension.

* * * * *